United States Patent
Bando et al.

(10) Patent No.: US 8,436,193 B2
(45) Date of Patent: May 7, 2013

(54) METHOD FOR MANUFACTURING SULFOLENE COMPOUND AND METHOD FOR MANUFACTURING SULFOLANE COMPOUND

(75) Inventors: Seiji Bando, Hyogo (JP); Hisaaki Kanda, Hyogo (JP); Yuichi Onoda, Hyogo (JP); Masayoshi Miyada, Hyogo (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 160 days.

(21) Appl. No.: 13/131,471

(22) PCT Filed: Nov. 30, 2009

(86) PCT No.: PCT/JP2009/070118
§ 371 (c)(1),
(2), (4) Date: Jul. 25, 2011

(87) PCT Pub. No.: WO2010/064605
PCT Pub. Date: Jun. 10, 2010

(65) Prior Publication Data
US 2011/0288307 A1  Nov. 24, 2011

(30) Foreign Application Priority Data

| Dec. 2, 2008 | (JP) | ................................ 2008-307567 |
| Dec. 2, 2008 | (JP) | ................................ 2008-307689 |
| Dec. 16, 2008 | (JP) | ................................ 2008-319039 |

(51) Int. Cl.
*C07D 333/48* (2006.01)
(52) U.S. Cl.
USPC ........................................................ 549/87
(58) Field of Classification Search ............... 549/87
See application file for complete search history.

(56) References Cited

U.S. PATENT DOCUMENTS

| 5,290,953 A | 3/1994 | Clark, Jr. et al. |
| 2003/0215745 A1 | 11/2003 | Fujimaki |

FOREIGN PATENT DOCUMENTS

| JP | 6-321936 | 11/1994 |
| JP | 7-017970 | 1/1995 |
| JP | 2003-335814 | 11/2003 |

OTHER PUBLICATIONS

Wu, et al., "Study on the deactivation of supported amorphous Ni-B catalyst in hydrogenation", Journal of Molecular Catalysis A: Chemical, vol. 273, 2007, pp. 277-283.

*Primary Examiner* — Taofiq A Solola
(74) *Attorney, Agent, or Firm* — Hamre, Schumann, Mueller & Larson, P.C.

(57) ABSTRACT

An object of the present invention is to provide a method for manufacturing a sulfolene compound, the method being capable of inhibiting generation of polymers. Another object of the present invention is to provide a method for manufacturing a sulfolane compound, the method being capable of controlling inhibition of hydrogenation catalyst activity and smoothly hydrogenating a sulfolene compound.

The present invention is a method for manufacturing a sulfolene compound represented by a formula (2), which comprises the step of reacting a conjugated diene compound represented by a formula (1) with sulfur dioxide in the presence of a metallocene compound:

[Chem. 1]

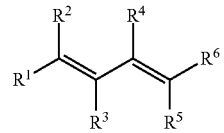

(1)

in the formula (1), $R^1$ to $R^6$ each independently represents a hydrogen atom or a C1 to C6 alkyl group,

[Chem. 2]

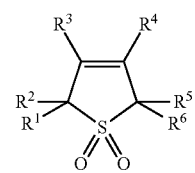

(2)

in the formula (2), $R^1$ to $R^6$ represent the same groups represented by $R^1$ to $R^6$ in the formula (1).

11 Claims, No Drawings

METHOD FOR MANUFACTURING SULFOLENE COMPOUND AND METHOD FOR MANUFACTURING SULFOLANE COMPOUND

TECHNICAL FIELD

The present invention relates to a method for manufacturing a sulfolene compound, the method being capable of inhibiting generation of polymers. In addition, the present invention relates to a method for manufacturing a sulfolane compound, the method being capable of controlling inhibition of hydrogenation catalyst activity and smoothly hydrogenating a sulfolene compound.

BACKGROUND ART

A sulfolane compound is used in a solvent for extraction of benzene, toluene, xylene, and the like, an acid-gas remover, a reaction solvent for an aromatic compound, and a solvent for manufacturing an electronic component. Known methods for manufacturing a sulfolane compound include a method comprising hydrogenating a sulfolene compound obtainable by reacting a conjugated diene compound with sulfur dioxide.

However, in the reaction for obtaining a sulfolene compound in common manufacturing of a sulfolane compound, there have been problems. For example, polymers may be generated to block pipes in the equipment. For another example, the activity of a hydrogenation catalyst may be inhibited by residual sulfur dioxide during a hydrogenation reaction of the sulfolene compound, leading to a prolonged reaction time and need for a large amount of an additional catalyst.

Various methods have been proposed to overcome such problems. In a method for manufacturing sulfolene, 4-t-butylcatechol functioning as a polymerization inhibitor is added to sulfur dioxide and reacts with butadiene to inhibit generation of polymers (Patent Document 1). In a method for manufacturing a sulfolane compound, after the reaction between butadiene and sulfur dioxide to produce a sulfolene compound using dimethyl amine as a polymerization inhibitor, inert gas is introduced to remove sulfur dioxide from the reaction system prior to a hydrogenation reaction for controlling inhibition of the hydrogenation catalyst activity by residual sulfur dioxide (Patent Document 2).

Patent Document 1: Japanese Kokai Publication No. Hei-07-17970(JP-A H07-17970)
Patent Document 2: Japanese Kokai Publication No. Hei-06-321936(JP-A H06-321936)

DISCLOSURE OF THE INVENTION

Problems to be Solved by the Invention

The method disclosed in Patent Document 1 effectively inhibits generation of polymers in manufacturing of sulfolene, but that effect is not always sufficiently exerted depending on reaction conditions. In the method disclosed in Patent Document 2, even though sulfur dioxide is removed prior to a hydrogenation reaction, dimethylamine used as a polymerization inhibitor problematically inhibits the hydrogenation reaction unless the dimethylamine is removed. In addition, the hydrogenation reaction problematically takes time even when a commercially available sulfolene compound is used as a starting material.

An object of the present invention is to provide a method for manufacturing a sulfolene compound, the method being capable of inhibiting generation of polymers. Another object of the present invention is to provide a method for manufacturing a sulfolane compound, the method being capable of controlling inhibition of hydrogenation catalyst activity and smoothly hydrogenating a sulfolene compound.

Means for Solving the Problems

The present invention provides a method for manufacturing a sulfolene compound represented by a formula (2), which comprises the step of reacting a conjugated diene compound represented by a formula (1) with sulfur dioxide in the presence of a metallocene compound.

[Chem. 1]

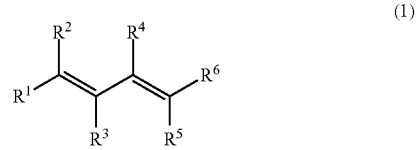

(1)

In the formula (1), $R^1$ to $R^6$ each independently represents a hydrogen atom or a C1 to C6 alkyl group.

[Chem. 2]

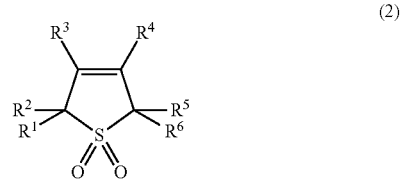

(2)

In the formula (2), $R^1$ to $R^6$ represent the same groups represented by $R^1$ to $R^6$ in the formula (1).

The present invention further provides a method for manufacturing a sulfolane compound represented by a formula (3), which comprises the steps of reacting a conjugated diene compound represented by a formula (1) with sulfur dioxide in the presence of a metallocene compound to produce a sulfolene compound represented by a formula (2), and hydrogenating the sulfolene compound in the presence of a hydrogenation catalyst.

[Chem. 3]

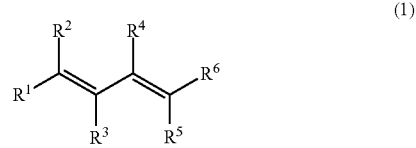

(1)

In the formula (1), $R^1$ to $R^6$ each independently represents a hydrogen atom or a C1 to C6 alkyl group.

[Chem. 4]

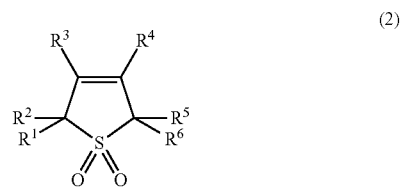

(2)

In the formula (2), $R^1$ to $R^6$ represent the same groups represented by $R^1$ to $R^6$ in the formula (1).

[Chem. 5]

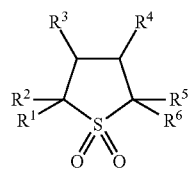

(3)

In the formula (3), $R^1$ to $R^6$ represent the same groups represented by $R^1$ to $R^6$ in the formula (1).

In addition, another aspect of the present invention provides a method for manufacturing a sulfolane compound represented by a formula (3), which comprises the step of hydrogenating a sulfolene compound represented by a formula (2) in the presence of a hydrogenation catalyst and at least one of a stabilizer and an alkali agent.

[Chem. 6]

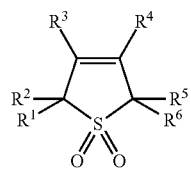

(2)

In the formula (2), $R^1$ to $R^6$ each independently represents a hydrogen atom or a C1 to C6 alkyl group.

[Chem. 7]

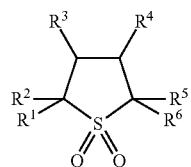

(3)

In the formula (3), $R^1$ to $R^6$ represent the same groups represented by $R^1$ to $R^6$ in the formula (2).

In the following, the present invention is described in detail. First, the method for manufacturing a sulfolene compound of the present invention is described in detail.

Specific examples of the conjugated diene compound represented by the formula (1) include 1,3-butadiene, 2-methyl-1,3-butadiene, 2-ethyl-1,3-butadiene, 2-propyl-1,3-butadiene, 2-butyl-1,3-butadiene, 2-isobutyl-1,3-butadiene, 2-tert-butyl-1,3-butadiene, 2-hexyl-1,3-butadiene, 2,3-dimethyl-1,3-butadiene, 2,3-diethyl-1,3-butadiene, 2,3-dibutyl-1,3-butadiene, 2-methyl-3-hexyl-1,3-butadiene, 2,4-hexadiene, 3-methyl-2,4-hexadiene, 3-hexyl-2,4-hexadiene, 3,4-dimethyl-2,4-hexadiene, 3,5-octadiene, 3-methyl-3,5-octadiene, 3,6-dimethyl-3,5-octadiene, 4,5-dimethyl-3,5-octadiene, 4,6-decadiene, 5-methyl-4,6-decadiene, and 5,6-dimethyl-4,6-decadiene. Among these, the conjugated diene compound to be used is preferably at least one compound selected from the group consisting of 1,3-butadiene, 2-methyl-1,3-butadiene, 2,3-dimethyl-1,3-butadiene, 2,3-diethyl-1,3-butadiene, 3,4-dimethyl-2,4-hexadiene, and the like.

In the reaction between the conjugated diene compound and sulfur dioxide, the amount of sulfur dioxide is not particularly limited. For example, the amount of sulfur dioxide is preferably 0.5 to 10 moles and more preferably 0.75 to 5 moles, for 1 mole of the conjugated diene compound. In this case, the amount of less than 0.5 moles may lower the yield of a sulfolene compound represented by the formula (2) (hereinafter, also simply referred to as a sulfolene compound). In contrast, the amount of more than 10 moles does not give sufficient effect for the used amount and is not economically reasonable.

Specific examples of the metallocene compound used in the reaction between the conjugated diene compound and sulfur dioxide include: ferrocene compounds such as ferrocene, methylferrocene, ethylferrocene, butylferrocene, tert-butylferrocene, 1,1'-dimethylferrocene, 1,1'-dibutylferrocene, acetylferrocene, and phenylferrocene; nickelocene compounds such as nickelocene; ruthenocene compounds such as ruthenocene; zirconocene compounds such as zirconocene; and titanocene compounds such as titanocene. Among these metallocene compounds, ferrocene compounds are preferably used. Particularly, ferrocene is preferably used. Each of these metallocene compounds may be used alone, or two or more of these may be used in combination.

Though not particularly limited, the amount of the metallocene compound is preferably 0.000001 to 0.1 moles and more preferably 0.00001 to 0.01 moles, for 1 mole of the conjugated diene compound. In this case, the amount of less than 0.000001 moles may increase generation of polymers to cause problems such as pipe obstruction in the manufacturing equipment. Removal of such polymers may consume a great deal of time. In contrast, the amount of more than 0.1 moles does not give sufficient effect for the used amount and is not economically reasonable.

A solvent is not necessarily used in the reaction between the conjugated diene compound and sulfur dioxide, and is optionally used, for example, in a case where stirring is insufficient because the raw material is solid or the reaction liquid is highly viscous. Examples of the solvent include: alcohols such as methanol, ethanol, propanol, isopropanol, and butanol; sulfone compounds such as sulfolane, 2-methyl sulfolane, and 3-methyl sulfolane; sulfoxide compounds such as dimethyl sulfoxide; organic amide compounds such as N-methyl-2-pyrolidone, and N,N-dimethylformamide; and water.

The reaction temperature of the reaction between the conjugated diene compound and sulfur dioxide is preferably 50° C. to 150° C. and more preferably 70° C. to 130° C.

The pressure in the reaction vessel used for the reaction between the conjugated diene compound and sulfur dioxide is commonly 0.2 to 6.5 MPa, though it depends on the reaction temperature and the like. Here, the pressure in the reaction vessel in the present description is a gauge pressure that sets the atmospheric pressure as the standard (atmospheric pressure=0).

The reaction time of the reaction between the conjugated diene compound and sulfur dioxide is commonly 0.5 to 50 hours, though it depends on the reaction temperature and the like.

After the reaction between the conjugated diene compound and sulfur dioxide, the residual gas in the reaction vessel is purged and the resulting reaction liquid is cooled. In this manner, a sulfolene compound represented by the formula (2) is obtained. Alternatively, after the purge of the residual gas in the reaction vessel, a solvent such as water may be added thereto and a sulfolene compound represented by the formula (2) may be obtained in the form of a solution. After the solution is cooled so that a sulfolene compound is precipitated, the sulfolene compound may be isolated by filtration and the like.

Specific examples of the sulfolene compound represented by the formula (2) include 3-sulfolene, 3-methyl-3-sulfolene, 3-ethyl-3-sulfolene, 3-propyl-3-sulfolene, 3-butyl-3-sulfolene, 3-isobutyl-3-sulfolene, 3-tert-butyl-3-sulfolene, 3-hexyl-3-sulfolene, 3,4-dimethyl-3-sulfolene, 3,4-diethyl-3-sulfolene, 3,4-dibutyl-3-sulfolene, 3-hexyl-4-methyl-3-sulfolene, 2,5-dimethyl-3-sulfolene, 2,3,5-trimethyl-3-sulfolene, 2,5-dimethyl-3-hexyl-3-sulfolene, 2,3,4,5-tetramethyl-3-sulfolene, 2,5-diethyl-3-sulfolene, 2,5-diethyl-2-methyl-3-sulfolene, 2,5-diethyl-2,5-dimethyl-3-sulfolene, 2,5-diethyl-3,4-dimethyl-3-sulfolene, 2,5-diethyl-3-sulfolene, 2,5-dipropyl-3-sulfolene, 2,5-dipropyl-3-methyl-3-sulfolene, and 2,5-dipropyl-3,4-dimethyl-3-sulfolene.

Hydrogenation of the above solution without isolation of the sulfolene compound efficiently produces a sulfolane compound represented by the formula (3) (hereinafter, also simply referred to as a sulfolane compound).

Another aspect of the present invention is a method for manufacturing a sulfolane compound represented by a formula (3), which comprises the steps of reacting a conjugated diene compound represented by a formula (1) with sulfur dioxide in the presence of a metallocene compound to produce a sulfolene compound represented by a formula (2), and hydrogenating the sulfolene compound in the presence of a hydrogenation catalyst.

[Chem. 8]

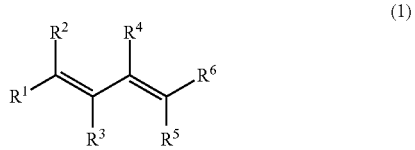

(1)

In the formula (1), $R^1$ to $R^6$ each independently represents a hydrogen atom or a C1 to C6 alkyl group.

[Chem. 9]

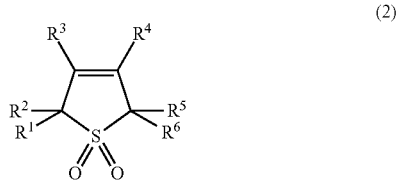

(2)

In the formula (2), $R^1$ to $R^6$ represent the same groups represented by $R^1$ to $R^6$ in the formula (1).

[Chem. 10]

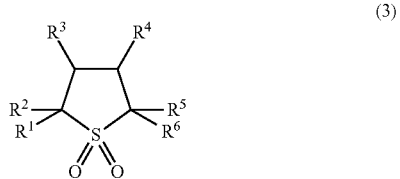

(3)

In the formula (3), $R^1$ to $R^6$ represent the same groups represented by $R^1$ to $R^6$ in the formula (1).

In the following, the method for manufacturing a sulfolane compound of the present invention is described in detail.

In the method for manufacturing a sulfolane compound of the present invention, residual sulfur dioxide which inhibits hydrogenation catalyst activity is preferably removed by deaeration and the like, prior to hydrogenation of the sulfolene compound. The concentration of residual sulfur dioxide is preferably 50 ppm or less. In a case where the concentration of residual sulfur dioxide is more than 50 ppm, the hydrogenation reaction may not sufficiently proceed.

A hydrogenation catalyst used in the method for manufacturing a sulfolane compound of the present invention is not particularly limited, provided that it is one commonly used in a catalytic hydrogenation reaction. Examples thereof include: metals such as iron, cobalt, nickel, copper, palladium, rhodium, ruthenium and platinum; and metal compounds. It may be used, for example, in the form of: fines; a catalyst supported on a carrier such as activated carbon, aluminum oxide, silica gel, diatom earth, and zeolite; or a complex with phosphine, amine, or the like. Specific examples thereof include Raney nickel, nickel carbon, palladium carbon, palladium chloride, palladium acetate, ruthenium carbon, rhodium carbon, and platinum carbon. Each of these hydrogenation catalysts may be used alone, or two or more of these may be used in combination.

Though not particularly limited, the amount of the hydrogenation catalyst is preferably 0.05 to 6.0 parts by weight, more preferably 0.1 to 3.0 parts by weight, and further preferably 0.2 to 3.0 parts by weight, for 100 parts by weight of the sulfolene compound. In this case, the amount of less than 0.05 parts by weight may not allow the reaction to sufficiently proceed to be completed, resulting in the lower yield of a sulfolane compound. The amount of more than 6.0 parts by weight does not give sufficient effect for the used amount and is not economically reasonable.

A reaction solvent used in the hydrogenation reaction include: alcohols such as methanol, ethanol, isopropanol, propanol, butanol, and pentanol; sulfone compounds such as sulfolane, 2-methylsulfolane, 3-methylsulfolane, and 3-ethylsulfolane; sulfoxide compounds such as dimethyl sulfoxide; organic amide compounds such as N-methyl-2-pyrrolidone and N,N-dimethylformamide; and water. Among these, water is preferably used from the standpoint of price and handleability.

Though not particularly limited, the amount of the reaction solvent is preferably 10 to 10000 parts by weight, more preferably 10 to 8000 parts by weight, further preferably 20 to 5000 parts by weight, and particularly preferably 20 to 4000 parts by weight, for 100 parts by weight of the sulfolene compound. In this case, the amount less than 10 parts by weight may make the reaction proceed not smoothly due to precipitation of the raw materials and the like, resulting in the lower yield of a sulfolane compound. In contrast, the amount of more than 10000 parts by weight does not give sufficient effect for the used amount because that amount deteriorates the volumetric efficiency and is not economically reasonable.

An exemplary method of the hydrogenation reaction comprises the step of, for example, introducing hydrogen gas into the reaction vessel to make the reaction proceed under a hydrogen atmosphere.

The reaction temperature of the reaction hydrogenating the sulfolene compound is preferably 0° C. to 150° C., and more preferably 15° C. to 100° C. The reaction temperature of lower than 0° C. may not allow the reaction to sufficiently proceed to be completed, resulting in the lowered yield of a sulfolane compound. In contrast, the reaction temperature of higher than 150° C. may cause generation of by-products due to decomposition of the sulfolene compound, resulting in the lowered yield of a sulfolane compound.

The pressure in the reaction vessel during the reaction for hydrogenating the sulfolene compound is commonly 0 to 6 MPa under a hydrogen atmosphere, though it depends on the reaction temperature and the like.

The reaction time of the reaction for hydrogenating the sulfolene compound is commonly 50 to 300 minutes, though it depends on the reaction temperature and the like.

After the reaction for hydrogenating the sulfolene compound, residual hydrogen gas and the like in the reaction vessel are purged and the resulting reaction liquid is filtered. Then, the solvent is removed therefrom by distillation under reduced pressure. In this manner, a sulfolane compound represented by the formula (3) is obtained.

Examples of the sulfolane compound represented by the formula (3) include sulfolane, 3-methyl sulfolane, 3-ethyl sulfolane, 3-propyl sulfolane, 3-butyl sulfolane, 3-isobutyl sulfolane, 3-tert-butyl sulfolane, 3-hexyl sulfolane, 3,4-dimethyl sulfolane, 3,4-diethyl sulfolane, 3,4-dibutyl sulfolane, 3-hexyl-4-methyl sulfolane, 2,5-dimethyl sulfolane, 2,3,5-trimethyl sulfolane, 2,5-dimethyl-3-hexyl sulfolane, 2,3,4,5-tetramethyl sulfolane, 2,5-diethyl sulfolane, 2,5-diethyl-2-methyl sulfolane, 2,5-diethyl-2,5-dimethyl sulfolane, 2,5-diethyl-3,4-dimethyl sulfolane, 2,5-diethyl sulfolane, 2,5-dipropyl sulfolane, 2,5-dipropyl-3-methyl sulfolane, and 2,5-dipropyl-3,4-dimethyl sulfolane.

Another aspect of the present invention provides a method for manufacturing a sulfolane compound represented by a formula (3), which comprises the step of hydrogenating a sulfolene compound represented by a formula (2) in the presence of a hydrogenation catalyst and at least one of a stabilizer and an alkali agent to produce the sulfolane compound.

[Chem. 11]

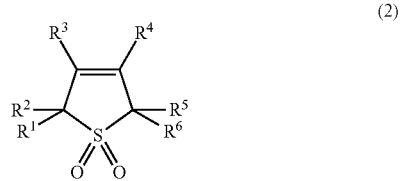

(2)

In the formula (2), $R^1$ to $R^6$ represent the same groups represented by $R^1$ to $R^6$ in the formula (1).

[Chem. 12]

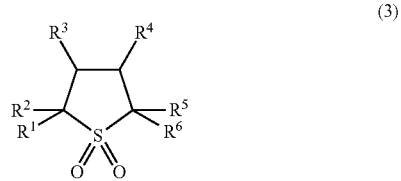

(3)

In the formula (3), $R^1$ to $R^6$ represent the same groups represented by $R^1$ to $R^6$ in the formula (1).

The sulfolene compound represented by the formula (2) in the method for manufacturing a sulfolane compound according to another aspect of the present invention is not particularly limited. The compound manufactured by the method for manufacturing a sulfolene compound of the present invention is preferably used.

A method for hydrogenating the sulfolene compound represented by the formula (2) in the method for manufacturing a sulfolane compound according to another aspect of the present invention is similar to the method for manufacturing a sulfolane compound of the present invention, except that the stabilizer and/or the alkali agent are used. Therefore, the description is only given about the stabilizer and the alkali agent.

In the method for manufacturing a sulfolane compound according to another aspect of the present invention, use of a stabilizer allows a hydrogenation reaction of a sulfolene compound to proceed smoothly.

Specific examples of the stabilizer include: phenol compounds such as 4-t-butylcatechol, hydroquinone, 4-t-butylhydroquinone, 2,6-di-t-butyl-p-cresol, hydroquinone monomethylether, butylhydroxyanisole, pyrogallol, 2,4-dinitrophenol, and 2,4,6-trihydroxybenzene; quiones such as p-benzoquinone, chloranil, and trimethylquinone; metallocene compounds such as ferrocene, methylferrocene, acetylferrocene, phenylferrocene, nickelocene, ruthenocene, zirconocene, and titanocene; and methoxyanisole.

Among these, 4-t-butylcatechol, hydroquinone, 2,6-di-t-butyl-p-cresol, and ferrocene are preferably used from the standpoint of price and availability. Further, 4-t-butylcatechol and ferrocene are more preferably used. Each of these stabilizers may be used alone, or two or more of these may be used in combination.

Though not particularly limited, the amount of the stabilizer is preferably 0.0001 to 0.1 moles and more preferably 0.001 to 0.05 moles, for 1 mole of the sulfolene compound. In this case, the amount of less than 0.0001 moles may make the hydrogenation reaction of the sulfolene compound take longer time and require a large amount of a hydrogenation catalyst. In contrast, the amount of more than 0.1 moles does not give sufficient effect for the used amount and is not economically reasonable.

The reason why use of the stabilizer allows a hydrogenation reaction of a sulfolene compound to proceed smoothly is not clear. The following function is presumably carried out by the stabilizer. Sulfur dioxide generated by thermal decomposition of a sulfolene compound and the like are likely to inhibit the activity of a coexisting hydrogenation catalyst. The stabilizer may suppress the thermal decomposition of sulfolene and reduce the inhibition of the hydrogenation catalyst activity by sulfur dioxide.

In the method for manufacturing a sulfolane compound according to another aspect of the present invention, use of an alkali agent allows a hydrogenation reaction of a sulfolene compound to proceed smoothly.

Specific examples of the alkali agent include magnesium hydroxide, magnesium oxide, calcium hydroxide, calcium oxide, barium hydroxide, and barium oxide. Among these, magnesium hydroxide and magnesium oxide are preferably used as they are hardly soluble in a later-described reaction solvent and prevent the reaction liquid from becoming excessively alkaline. Each of these alkali agents may be used alone, or two or more of these may be used in combination.

Though not particularly limited, the amount of the alkali agent is preferably 0.1 to 1.0 parts by weight and more preferably 0.2 to 0.5 parts by weight, for 100 parts by weight of the sulfolene compound. In this case, the amount of less than 0.1 parts by weight may make a hydrogenation reaction proceed not smoothly, resulting in the lower yield of a sulfolane compound. The amount of more than 1.0 part by weight does not give sufficient effect for the used amount and is not economically reasonable.

The reason why use of the alkali agent allows a hydrogenation reaction of a sulfolene compound to proceed smoothly is not clear. The following function is presumably carried out by the alkali agent. Sulfur dioxide generated by thermal decomposition of a sulfolene compound and the like are likely to acidize the reaction liquid to allow a metal component of a hydrogenation catalyst to easily dissolve in the reaction liquid, leading to the lowered catalytic activity. The alkali agent may suppress dissolution of the metal component by adjusting pH of the reaction solution to neutral to alkaline. The pH of the reaction liquid is preferably weakly alkaline (e.g. less than pH 10) from the standpoint of preventing a side reaction. In addition, another function presumably carried out by the alkali agent is that the reaction between sulfur dioxide and the alkali agent produces sulfite salts and the like which are hardly soluble in the reaction solvent to reduce inhibition of the catalytic activity. These functions act synergistically to allow a hydrogenation reaction to proceed smoothly.

Effect of the Invention

The present invention provides a method for manufacturing a sulfolene compound, the method being capable of inhibiting generation of polymers. In addition, the present invention provides a method for manufacturing a sulfolane compound, the method being capable of controlling inhibition of hydrogenation catalyst activity and smoothly hydrogenating a sulfolene compound.

MODE FOR CARRYING OUT THE INVENTION

Hereinafter, the present invention will be described in more detail by way of examples, but the present invention is not limited to these examples.

Example 1

An amount of 0.186 g (1.0 mmol) of ferrocene was fed into a 500-mL stainless autoclave equipped with a stirrer, a thermometer, a pressure gauge, and a heater. Then, 77 g of sulfur dioxide was charged therein. Next, the autoclave was heated to 100° C. and 54 g (1.0 mol) of 1,3-butadiene was injected thereto at a rate of 0.38 g/min using a pump. The mixture was stirred for one hour at 100° C. During the stirring, the pressure inside the autoclave was 2.7 to 0.7 MPa.

After the pressure inside the autoclave was discharged, 150 g of water was added and the autoclave was cooled to 60° C. The autoclave contents were filtered through a filter paper to give a 3-sulfolene aqueous solution. The amount of 3-sulfolene in the obtained aqueous solution was measured using liquid chromatography and the measurement was 103 g (0.87 mol). The yield from 1,3-butadiene was 87%. It is to be noted that polymers were not found on the filter paper used in filtering.

All of the obtained 3-sulfolene aqueous solution was fed into a 500-ml conical flask and 70 g of water was added thereto. The solution was warmed to 35° C. and bubbled with air at a rate of 100 ml/min for one hour. In this manner, sulfur dioxide dissolved in the 3-sulfolene aqueous solution was removed. The concentration of sulfur dioxide in the 3-sulfolene aqueous solution was measured using ion chromatography and the measurement was 31 ppm.

Next, 200 g of the obtained 3-sulfolene aqueous solution (3-sulfolene content of 64 g (0.54 mol)) and 1.04 g (0.52 g of pure nickel) of Raney nickel (water content of 50%) were fed into a 500-mL stainless autoclave equipped with a stirrer, a thermometer, a pressure gauge, and a heater. The temperature inside the autoclave was maintained at 35° C. Hydrogen was introduced into the autoclave until the pressure gauge read 1.0 MPa. The reaction was initiated while the mixture was stirred at 1000 rpm. Hydrogen was consumed in the hydrogenation reaction and was additionally supplied, when the reading by the pressure gauge lowered to 0.9 MPa, to pressurize to 1.0 MPa. This operation was repeated until the pressure stopped lowering, at which the reaction was determined to be completed. As a result, the reaction time from the start to the completion of the reaction was 78 minutes. After the reaction completed, the reaction rate of hydrogenation was measured using gas chromatography. The measurement clarified that 3-sulfolene was vanished and the reaction was 100% progressed. Table 1 shows the measurements of the amount of generated polymers and the reaction time of hydrogenation.

Example 2

Except that the amount of ferrocene used in manufacturing of sulfolene was changed to 0.019 g (0.10 mmol), a 3-sulfolene aqueous solution was prepared in the same manner as in Example 1. The amount of 3-sulfolene in the obtained aqueous solution was 104 g (0.88 mol) and the yield from 1,3-butadiene was 88%. Polymers were not found on the filter paper after filtering the 3-sulfolene aqueous solution. Next, the obtained 3-sulfolene aqueous solution was hydrogenated in the same manner as in Example 1. The reaction time was 98 minutes and the reaction was 100% progressed. Table 1 shows the measurements of the amount of generated polymers and the reaction time of hydrogenation.

Example 3

Except that the amount of ferrocene used in manufacturing of sulfolene was changed to 0.002 g (0.01 mmol), a 3-sulfolene aqueous solution was prepared in the same manner as in Example 1. The amount of 3-sulfolene in the obtained aqueous solution was 104 g (0.88 mol) and the yield from 1,3-butadiene was 88%. An amount of 0.001 g of polymers was found on the filter paper after filtering the 3-sulfolene aqueous solution. Next, the obtained 3-sulfolene aqueous solution was hydrogenated in the same manner as in Example 1. The reaction time was 90 minutes and the reaction was 100% progressed. Table 1 shows the measurements of the amount of generated polymers and the reaction time of hydrogenation.

Comparative Example 1

Except that 0.166 g (1.0 mmol) of 4-t-butylcatechol was used instead of 0.186 g (1.0 mmol) of ferrocene used in manufacturing of sulfolene, a 3-sulfolene aqueous solution was prepared in the same manner as in Example 1. The amount of 3-sulfolene in the obtained aqueous solution was 87 g (0.75 mol) and the yield from 1,3-butadiene was 75%. An amount of 3.8 g of polymers was found on the filter paper after filtering the 3-sulfolene aqueous solution. Next, the obtained 3-sulfolene aqueous solution was hydrogenated in the same manner as in Example 1. The reaction time was 70 minutes and the reaction was 100% progressed. Table 1 shows the measurements of the amount of generated polymers and the reaction time of hydrogenation.

Comparative Example 2

Except that 0.045 g (1.0 mmol) of dimethylamine was used instead of 0.186 g (1.0 mmol) of ferrocene used in manufacturing of sulfolene, a 3-sulfolene aqueous solution was prepared in the same manner as in Example 1. The amount of 3-sulfolene in the obtained aqueous solution was 100 g (0.85 mol) and the yield from 1,3-butadiene was 85%. An amount of 0.1 g of polymers was found on the filter paper after filtering the 3-sulfolene aqueous solution. Next, the obtained 3-sulfolene aqueous solution was hydrogenated in the same manner as in Example 1. The hydrogen pressure did not stop lowering in 340 minutes of the reaction time. At that time, the reaction rate was 75%. Table 1 shows the measurements of the amount of generated polymers and the reaction time of hydrogenation.

Comparative Example 3

Except that 0.13 g (1.0 mmol) of iron (II) chloride was used in manufacturing of sulfolene instead of 0.186 g (1.0 mmol) of ferrocene, a 3-sulfolene aqueous solution was prepared in the same manner as in Example 1. The amount of 3-sulfolene in the obtained aqueous solution was 103 g (0.85 mol) and the yield from 1,3-butadiene was 85%. An amount of 0.01 g of polymers was found on the filter paper after filtering the 3-sulfolene aqueous solution. Next, the obtained 3-sulfolene aqueous solution was hydrogenated in the same manner as in Example 1. The hydrogen pressure did not stop lowering in 240 minutes of the reaction time. At that time, the reaction rate was 57%. Table 1 shows the measurements of the amount of generated polymers and the reaction time of hydrogenation.

TABLE 1

| | Polymerization inhibitor | Amount of polymerization inhibitor | Amount of generated polymer | Reaction time of hydrogenation |
|---|---|---|---|---|
| Example 1 | Ferrocene | 1.0 mmol | 0 g | 78 min. |
| Example 2 | Ferrocene | 0.1 mmol | 0 g | 98 min. |
| Example 3 | Ferrocene | 0.01 mmol | 0.001 g | 90 min. |
| Comparative Example 1 | t-Butyl-catechol | 1.0 mmol | 3.8 g | 70 min. |
| Comparative Example 2 | Dimethylamine | 1.0 mmol | 0.1 g | not completed in 340 min. |
| Comparative Example 3 | Iron (II) chloride | 1.0 mmol | 0.01 g | not completed in 240 min. |

Comparison of Example 1 with Comparative Example 1 shows that use of a metallocene compound as a polymerization inhibitor inhibits generation of polymers. Comparison of Example 1 with Comparative Examples 2 and 3 shows that use of 3-sulfolene manufactured using a metallocene compound reduces the reaction time of hydrogenation to allow the hydrogenation reaction to proceed smoothly.

Example 4

An amount of 64 g (0.54 mol) of 3-sulfolene (product of Tokyo Chemical Industry Co., Ltd.) and 136 g of water were fed into a 500-mL stainless autoclave equipped with a stirrer, a thermometer, a pressure gauge, and a heater, and the 3-sulfolene was dissolved. To the solution, 0.1 g (0.6 mmol) of 4-t-butylcatechol and 1.04 g (0.52 g of pure nickel) of Raney nickel (water content of 50%) were added and the temperature of the solution was maintained at 35° C. Hydrogen was introduced into the autoclave until the pressure gauge read 1.0 MPa. The reaction was initiated while the mixture was stirred at 1000 rpm. Hydrogen was consumed in the hydrogenation reaction and was additionally supplied, when the reading by the pressure gauge lowered to 0.9 MPa, to pressurize to 1.0 MPa. This operation was repeated until the pressure stopped lowering, at which the reaction was determined to be completed. As a result, the reaction time from the start to the completion of the reaction was 78 minutes. After the reaction completed, the reaction rate of hydrogenation was measured using gas chromatography. The measurement clarified that 3-sulfolene was vanished and the reaction was 100% progressed. Table 2 shows the results.

Example 5

An amount of 0.40 g (8.8 mmol) of dimethylamine was fed into a 500-mL stainless autoclave equipped with a stirrer, a thermometer, a pressure gauge, and a heater. Then, 154 g (2.4 mol) of sulfur dioxide was charged therein. Next, the autoclave was heated to 100° C. and 108 g (2.0 mol) of 1,3-butadiene was injected thereto at a rate of 0.76 g/min using a pump. The mixture was stirred for one hour at 100° C. During the stirring, the pressure inside the autoclave was 2.7 to 0.7 MPa.

After the pressure inside the autoclave was discharged, the autoclave contents were introduced into a 1-L flask and 300 g of water was added thereto. The solution was cooled to 60° C. and filtered through a filter paper to give a 3-sulfolene aqueous solution. The amount of 3-sulfolene in the obtained aqueous solution was measured using liquid chromatography and the measurement was 204 g (1.72 mol). The yield from 1,3-butadiene was 86%.

All of the obtained 3-sulfolene aqueous solution was fed into a 1-L flask and 140 g of water was added thereto. The solution was warmed to 35° C. and bubbled with air at a rate of 200 mL/min for one hour. In this manner, sulfur dioxide dissolved in the 3-sulfolene aqueous solution was removed. The concentration of sulfur dioxide in the 3-sulfolene aqueous solution was measured using ion chromatography and the measurement was 10 ppm.

Next, 200 g of the obtained 3-sulfolene aqueous solution (3-sulfolene content of 63 g (0.53 mol)) and 0.3 g (1.8 mmol) of 4-t-butylcatechol and 1.04 g (0.52 g of pure nickel) of Raney nickel (water content of 50%) were fed into a 500-mL stainless autoclave equipped with a stirrer, a thermometer, a pressure gauge, and a heater. The temperature inside the autoclave was maintained at 35° C. Hydrogen gas was introduced into the autoclave until the pressure gauge read 1.0 MPa. The reaction was initiated while the mixture was stirred at 1000 rpm. Hydrogen was consumed in the hydrogenation reaction and was additionally supplied, when the reading by the pressure gauge lowered to 0.9 MPa, to pressurize to 1.0 MPa. This operation was repeated until the pressure stopped lowering, at which the reaction was determined to be completed. As a result, the reaction time from the start to the completion of the reaction was 123 minutes. After the reaction completed, the reaction rate of hydrogenation was measured using gas chromatography. The measurement clarified that 3-sulfolene was vanished and the reaction was 100% progressed. Table 2 shows the results.

Example 6

Except that the amount of 4-t-butylcatechol used in the hydrogenation reaction of 3-sulfolene was changed to 1.0 g (6.0 mmol), the hydrogenation reaction was conducted in the same manner as in Example 5. As a result, the reaction time was 88 minutes and the reaction was 100% progressed. Table 2 shows the results.

Example 7

Except that 0.3 g (1.6 mmol) of ferrocene was used in stead of 0.3 g (1.8 mmol) of 4-t-butylcatechol used in the hydrogenation reaction of 3-sulfolene, the hydrogenation reaction was conducted in the same manner as in Example 5. As a result, the reaction time was 140 minutes and the reaction was 100% progressed. Table 2 shows the results.

Comparative Example 4

Except that 0.1 g (0.6 mmol) of 4-t-butylcatechol used in the hydrogenation reaction of 3-sulfolene was not used, the hydrogenation reaction was conducted in the same manner as in Example 4. As a result, the reaction time was 101 minutes and the reaction was 100% progressed. Table 2 shows the results.

Comparative Example 5

Except that 0.3 g (1.8 mmol) of 4-t-butylcatechol used in the hydrogenation reaction of 3-sulfolene was not used, the hydrogenation reaction was conducted in the same manner as in Example 5. As a result, the hydrogen pressure did not stop lowering in 340 minutes of the reaction time. At that time, the reaction rate was 75%. Table 2 shows the results.

TABLE 2

|  | Stabilizer | The amount of stabilizer | Reaction time of hydrogenation |
| --- | --- | --- | --- |
| Example 4 | 4-t-Butylcatechol | 0.6 mmol | 78 min. |
| Example 5 | 4-t-Butylcatechol | 1.8 mmol | 123 min. |
| Example 6 | 4-t-Butylcatechol | 6.0 mmol | 88 min. |
| Example 7 | Ferrocene | 1.6 mmol | 140 min. |
| Comparative Example 4 | — | — | 101 min. |
| Comparative Example 5 | — | — | not completed in 340 min. |

Comparison of Example 4 with Comparative Example 4 and comparison of Examples 5 to 7 with Comparative Example 5 show that use of a stabilizer reduces the reaction time of hydrogenation of sulfolene to allow the hydrogenation reaction to proceed smoothly.

Example 8

An amount of 64 g (0.54 mol) of 3-sulfolene (product of Tokyo Chemical Industry Co., Ltd.) and 136 g of water were fed into a 500-mL stainless autoclave equipped with a stirrer, a thermometer, a pressure gauge, and a heater, and the 3-sulfolene was dissolved. To the solution, 0.30 g (5.14 mmol) of magnesium hydroxide was added and the mixture was stirred at 25° C. to 35° C. for about five minutes. Then, 0.48 g (0.24 g of pure nickel) of Raney nickel (water content of 50%) was further added. Next, hydrogen was introduced into the autoclave until the pressure gauge read 1.0 MPa and a hydrogenation reaction was started. Hydrogen was consumed in the hydrogenation reaction and was additionally supplied, when the reading by the pressure gauge lowered to 0.9 MPa, to pressurize to 1.0 MPa. This operation was repeated until the pressure stopped lowering, at which the reaction was determined to be completed. As a result, the reaction time from the start to the completion of the reaction was 140 minutes. After the reaction completed, the reaction rate of hydrogenation was measured using gas chromatography. The measurement clarified that 3-sulfolene was vanished and the reaction was 100% progressed. Table 3 shows the results.

Example 9

Except that 0.30 g (7.44 mmol) of magnesium oxide was used instead of 0.30 g of magnesium hydroxide used in the hydrogenation reaction of 3-sulfolene, the hydrogenation reaction was conducted in the same manner as in Example 8. As a result, the reaction time was 117 minutes and the reaction was 100% progressed. Table 3 shows the results.

Example 10

Except that 200 g of the 3-sulfolene aqueous solution (3-sulfolene content 64 g (0.54 mol)) obtained in Example 2 was used instead of 64 g (0.54 mol) of 3-sulfolene (product of Tokyo Chemical Industry Co., Ltd.) and 136 g of water, the hydrogenation reaction was conducted in the same manner as in Example 8. As a result, the reaction time was 120 minutes and the reaction was 100% progressed. Table 3 shows the results.

Comparative Example 6

Except that 0.30 g of magnesium hydroxide used in the hydrogenation reaction of 3-sulfolene was not used, the hydrogenation reaction was conducted in the same manner as in Example 8. As a result, the reaction time was 365 minutes and the reaction was 100% progressed. Table 3 shows the results.

Comparative Example 7

Except that 0.30 g of magnesium hydroxide used in the hydrogenation reaction of 3-sulfolene was not used and 0.48 g (0.24 g of pure nickel) of Raney nickel (water content of 50%) was changed to 0.96 g (0.48 g of pure nickel) of Raney nickel (water content of 50%), the hydrogenation reaction was conducted in the same manner as in Example 8. As a result, the reaction time was 146 minutes and the reaction was 100% progressed. Table 3 shows the results.

TABLE 3

|  | Alkali agent | Amount of alkali agent | Hydrogenation catalyst | Amount of hydrogenation catalyst | Reaction time of hydrogenation |
| --- | --- | --- | --- | --- | --- |
| Example 8 | Magnesium hydroxide | 0.3 g | Raney nickel | 0.24 g | 140 min. |
| Example 9 | Magnesium oxide | 0.3 g | Raney nickel | 0.24 g | 117 min. |
| Example 10 | Magnesium hydroxide | 0.3 g | Raney nickel | 0.24 g | 120 min. |
| Comparative Example 6 | — | — | Raney nickel | 0.24 g | 365 min. |
| Comparative Example 7 | — | — | Raney nickel | 0.48 g | 146 min. |

Comparison of Examples 8 and 9 with Comparative Example 6 shows that use of an alkali agent in the hydrogenation reaction of 3-sulfolene reduces the reaction time of hydrogenation to allow the hydrogenation reaction to proceed smoothly. In addition, comparison of Examples 8 and 9 with Comparative Example 7 shows that use of an alkali agent allows the hydrogenation reaction to proceed smoothly even when the amount of a hydrogenation catalyst is small.

INDUSTRIAL APPLICABILITY

The present invention provides a method for manufacturing a sulfolene compound, the method being capable of inhibiting generation of polymers. In addition, the present invention provides a method for manufacturing a sulfolane compound, the method being capable of controlling inhibition of hydrogenation catalyst activity and smoothly hydrogenating a sulfolene compound.

The invention claimed is:

1. A method for manufacturing a sulfolene compound represented by a formula (2),
which comprises the step of reacting a conjugated diene compound represented by a formula (1) with sulfur dioxide in the presence of a metallocene compound:

[Chem. 1]

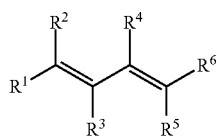
(1)

in the formula (1), $R^1$ to $R^6$ each independently represents a hydrogen atom or a C1 to C6 alkyl group,

[Chem. 2]

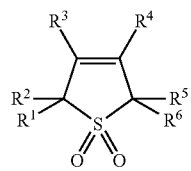
(2)

in the formula (2), $R^1$ to $R^6$ represent the same groups represented by $R^1$ to $R^6$ in the formula (1).

2. The method for manufacturing a sulfolene compound according to claim 1,
wherein the metallocene compound is a ferrocene compound.

3. The method for manufacturing a sulfolene compound according to claim 2,
wherein the ferrocene compound is ferrocene.

4. The method for manufacturing a sulfolene compound according to claim 1,
wherein the conjugated diene compound represented by the formula (1) is at least one conjugated diene compound selected from the group consisting of 1,3-butadiene, 2-methyl-1,3-butadiene, 2,3-dimethyl-1,3-butadiene, 2,3-diethyl-1,3-butadiene, and 3,4-dimethyl-2,4-hexadiene.

5. A method for manufacturing a sulfolane compound represented by a formula (3),
which comprises the steps of reacting a conjugated diene compound represented by a formula (1) with sulfur dioxide in the presence of a metallocene compound to produce a sulfolene compound represented by a formula (2), and hydrogenating the sulfolene compound in the presence of a hydrogenation catalyst:

[Chem. 3]

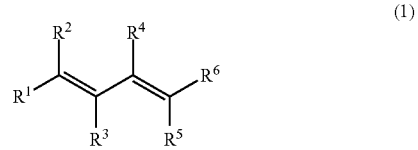
(1)

in the formula (1), $R^1$ to $R^6$ each independently represents a hydrogen atom or a C1 to C6 alkyl group,

[Chem. 4]

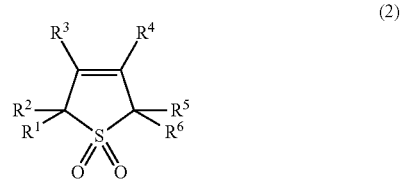
(2)

in the formula (2), $R^1$ to $R^6$ represent the same groups represented by $R^1$ to $R^6$ in the formula (1),

[Chem. 5]

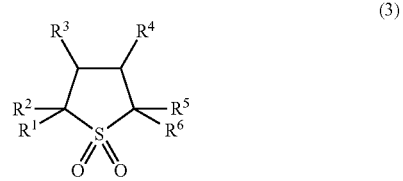
(3)

in the formula (3), $R^1$ to $R^6$ represent the same groups represented by $R^1$ to $R^6$ in the formula (1).

6. The method for manufacturing a sulfolane compound according to claim 5,
wherein the metallocene compound is a ferrocene compound.

7. The method for manufacturing a sulfolane compound according to claim 6,
wherein the ferrocene compound is ferrocene.

8. The method for manufacturing a sulfolane compound according to claim 5,
wherein the conjugated diene compound represented by the formula (1) is at least one conjugated diene compound selected from the group consisting of 1,3-butadiene, 2-methyl-1,3-butadiene, 2,3-dimethyl-1,3-butadiene, 2,3-diethyl-1,3-butadiene, and 3,4-dimethyl-2,4-hexadiene.

9. A method for manufacturing a sulfolane compound represented by a formula (3),
which comprises the step of hydrogenating a sulfolene compound represented by a formula (2) in the presence of a hydrogenation catalyst and at least one of a stabilizer and an alkali agent:

[Chem. 6]

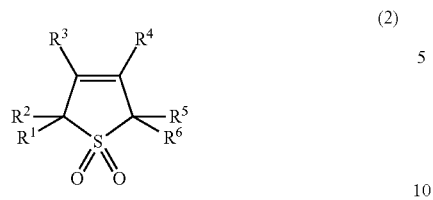

(2)

in the formula (2), $R^1$ to $R^6$ each independently represents a hydrogen atom or a C1 to C6 alkyl group,

[Chem. 7]

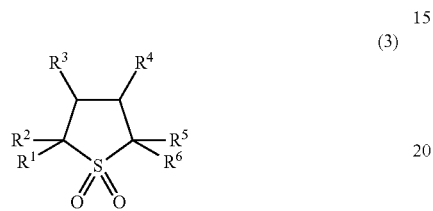

(3)

in the formula (3), $R^1$ to $R^6$ represent the same groups represented by $R^1$ to $R^6$ in the formula (2).

10. The method for manufacturing a sulfolane compound according to claim 9,
wherein the stabilizer is 4-t-butylcatechol or ferrocene.

11. The method for manufacturing a sulfolane compound according to claim 9,
wherein the alkali agent is magnesium hydroxide or magnesium oxide.

* * * * *